United States Patent [19]

Grabenkort

[11] Patent Number: 5,779,668

[45] Date of Patent: Jul. 14, 1998

[54] SYRINGE BARREL FOR LYOPHILIZATION, RECONSTITUTION AND ADMINISTRATION

[75] Inventor: Richard W. Grabenkort, Barrington, Ill.

[73] Assignee: Abbott Laboratories, Abbott Park, Ill.

[21] Appl. No.: 620,061

[22] Filed: Mar. 21, 1996

Related U.S. Application Data

[63] Continuation-in-part of Ser. No. 412,623, Mar. 29, 1995, abandoned.

[51] Int. Cl.$^6$ .................................................. A61M 37/00
[52] U.S. Cl. .......................... 604/89; 604/191; 604/218
[58] Field of Search ............................. 604/82–89, 91, 604/200–203, 236, 244, 191, 218, 190, 187, 228, 232

[56] References Cited

U.S. PATENT DOCUMENTS

| | | |
|---|---|---|
| 2,475,939 | 7/1949 | Applezweig .................... 604/201 |
| 3,255,752 | 6/1966 | Dick . |
| 3,477,432 | 11/1969 | Shaw . |
| 3,489,147 | 1/1970 | Shaw . |
| 3,621,843 | 11/1971 | Metten . |
| 3,678,931 | 7/1972 | Cohen . |
| 3,682,174 | 8/1972 | Cohen . |
| 3,754,644 | 8/1973 | Hampel . |
| 3,757,779 | 9/1973 | Rovinski ..................... 604/201 X |
| 3,838,689 | 10/1974 | Cohen . |
| 4,153,057 | 5/1979 | Köbel . |
| 4,171,698 | 10/1979 | Genese . |
| 4,172,457 | 10/1979 | Choksi et al. . |
| 4,243,080 | 1/1981 | Choksi et al. . |
| 4,581,016 | 4/1986 | Gettig ............................. 604/88 |
| 4,840,616 | 6/1989 | Banks . |
| 4,936,315 | 6/1990 | Lineback . |
| 4,957,637 | 9/1990 | Cornell . |
| 5,067,948 | 11/1991 | Haber et al. ..................... 604/213 |
| 5,088,996 | 2/1992 | Kopfer et al. . |
| 5,114,405 | 5/1992 | Winter . |
| 5,125,892 | 6/1992 | Drudik . |
| 5,135,507 | 8/1992 | Haber et al. . |
| 5,158,546 | 10/1992 | Haber et al. . |
| 5,176,639 | 1/1993 | Pozzi et al. ..................... 604/110 |
| 5,289,858 | 3/1994 | Grabenkort . |
| 5,298,024 | 3/1994 | Richmond ........................ 604/90 |
| 5,372,586 | 12/1994 | Haber et al. . |
| 5,407,431 | 4/1995 | Botich et al. . |
| 5,472,431 | 12/1995 | Godat et al. .................... 604/199 |
| 5,496,288 | 3/1996 | Sweeney . |
| 5,520,657 | 5/1996 | Sellers et al. .................. 604/191 |
| 5,569,193 | 10/1996 | Hofstetter et al. ............... 604/89 |

FOREIGN PATENT DOCUMENTS

| | | |
|---|---|---|
| 0 005 939 A | 12/1979 | European Pat. Off. . |
| 0005939 | 12/1979 | European Pat. Off. . |
| 0 298 585 A | 1/1989 | European Pat. Off. . |
| 0298585 | 1/1989 | European Pat. Off. . |
| 0302248 | 2/1989 | European Pat. Off. . |
| 0599649 | 6/1994 | European Pat. Off. . |
| 0695555 | 2/1996 | European Pat. Off. . |
| 9201485 | 2/1992 | WIPO . |
| WO 9201485 | 2/1992 | WIPO . |
| WO 92/10225 | 6/1992 | WIPO . |
| WO 9210225 | 6/1992 | WIPO . |

OTHER PUBLICATIONS

Search Report PCT/US96/04144.
Search Report PCT/US96/03913.

*Primary Examiner*—Mark Bockelman
*Assistant Examiner*—A. T. Nguyen
*Attorney, Agent, or Firm*—Neal D. Marcus

[57] ABSTRACT

The syringe system of the present invention includes a first or primary syringe barrel having a substantially closed end defining a delivery passage and an opposite open end. A removable closure seals the delivery passage of the first syringe barrel so as to define a container for containing a medical solution. A plurality of longitudinal channels are positioned on the inner surface of an enlarged diameter venting portion of the syringe barrel at the open end. A reciprocable stopper is provided for sealing the open end of the barrel so that the reciprocable stopper has a first position abutting the channels of the inner surface of the barrel so as to allow the medical solution to be lyophilized through the channels. The reciprocable stopper can then be longitudinally moved to a second position in the barrel in the in the direction of the delivery passage and beyond the channels to seal the lyophilized drug within the barrel.

29 Claims, 5 Drawing Sheets

SYRINGE BARREL FOR LYOPHILIZATION, RECONSTITUTION AND ADMINISTRATION

CROSS-REFERENCE TO RELATED APPLICATION

This is a continuation-in-part application of U.S. patent application Ser. No. 08/412,623, now abandoned, filed on Mar. 29, 1995.

TECHNICAL FIELD

The present invention relates generally to a syringe system for packaging, mixing and delivering a medical solution including a concentrated, preferably dry, drug component in one container and a liquid diluent component in a second container. More particularly, the present invention relates to a syringe system including a first primary syringe having a reciprocable stopper for sealing the open end of the syringe barrel so that a medical solution may be lyophilized, reconstituted with a liquid diluent in a second syringe, and administer from the primary syringe barrel.

BACKGROUND OF THE INVENTION

Modern healthcare facilities typically have a large number of drug and other medicaments on hand for IV administration to patients. Often these drugs, such as premixed solutions, may be administered without further preparation. For other drugs, it may be necessary or desirable to store the drug in a concentrated form, which may be either liquid or particulate in nature, to maintain the stability and potency of such drugs for a reasonable shelf life. Also, concentrated compositions facilitate efficient storage and handling since concentrates are not as bulky as solutions supplied in a premixed or ready to use concentration.

For example, the ADD-VANTAGE® drug delivery system sold by Abbott Laboratories, includes drug vials containing drug in powder form that has been lyophilized from a drug solution. The ADD-VANTAGE system also includes a mateable flexible bag for mixing a diluent with the dry drug in the vial. An outlet port is provided in the flexible bag for IV administration or syringe access to the reconstituted drug solution.

In certain instances, it may desirable to administer a reconstituted drug directly from a syringe without reconstituting the drug in an intermediate container such as the ADD-VANTAGE® flexible bag. The syringe system obviates the step of drawing the reconstituted solution from the mixing container into the syringe for administration.

Examples of two such drug and diluent syringe systems are described in the following copending patent applications, both assigned to Abbott Laboratories. A first application, entitled, "SYRINGE SYSTEM ACCOMMODATING SEPARATELY STORABLE PREFILLED CONTAINERS FOR TWO CONSTITUENTS", filed on Mar. 22, 1995, and assigned U.S. patent application Ser. No. 08/408,463 discloses a packaging and dispensing system including a drug in powder form packaged in a first syringe barrel. A second telescopically engagable syringe barrel contains a diluent. The disclosure of Ser. No. 08/408,463 is hereby incorporated by reference in this application. A second application entitled, "PREFILLED SYRINGE DRUG DELIVERY SYSTEM", filed on Mar. 22, 1995, and assigned U.S. patent application Ser. No. 08/408,436 discloses another two syringe barrel configuration for packaging a concentrated drug in powder form in a first of the two engagable syringe barrels. The disclosure of Ser. No. 08/408,436 is hereby incorporated by reference in this patent application.

Various concepts of packaging a concentrated drug and then mixing the drug and a diluent within a syringe barrel are known. However, none of the known syringe barrel and stopper constructions allow the drug to be lyophilized in the primary syringe barrel, reconstituted in the primary syringe barrel, and then administered from the primary syringe barrel while utilizing the same reciprocable stopper during all steps.

The present syringe system has been particularly configured to facilitate efficient and convenient lyophilization of a medical solution, reconstitution of the medical solution, and the administration of the drug solution from the same primary syringe barrel.

SUMMARY OF THE INVENTION

The syringe mixing system of the present invention includes a first or primary syringe barrel having an open end and an opposite delivery end defining a delivery passage. A removable closure seals the delivery passage of the barrel so as to define a container for containing a medical solution. At least one longitudinal channel is formed, and preferably a plurality of longitudinal channels are formed, on the interior surface of the first barrel. Preferably the channels are formed in a larger diameter venting portion at the open end of the first syringe barrel. A reciprocable stopper is provided for slidably sealing the open end of the first barrel. The reciprocable stopper has a first position located adjacent the venting channels of the primary syringe barrel at to allow the medical solution to be lyophilized through the channels. The slidable reciprocable stopper is then axially moved in the direction of the delivery passage to a second position in the first syringe barrel beyond the venting channels to seal the lyophilized drug within the primary syringe barrel.

In a preferred embodiment, the reciprocable stopper further includes a fluid transfer connector means or fluid communicating and connecting means for transfer of a liquid diluent from an associated second or diluent syringe barrel through the reciprocable stopper from the direction of the open end of the first syringe barrel. Various configurations for effecting fluid communication from the diluent syringe through the reciprocable stopper of the first syringe barrel include connection by a sharp cannula through a resealable elastomeric reciprocable stopper, or by a blunt cannula through a prepierced elastomeric reciprocable stopper, or by connection to a one-way valve mechanism through the reciprocable stopper. The later configuration includes a valve actuating connector on the diluent syringe. In a preferred configuration, the reciprocable stopper is elastomeric and includes a longitudinal slit defining a valve having resilient lips which are normally biased closed.

Preferably, the syringe system of the present invention includes a sterility maintenance sleeve in the expandable mixing chamber and a fluid transfer connector means that establishes a positive mechanical connection between the reciprocable stopper of the primary syringe barrel and the diluent syringe barrel. The reciprocable stopper preferably has a connecting construction, such as a cavity, for receiving part of a sterility maintenance sleeve, such as an enlarged head. The diluent syringe barrel is connectable to the sterility maintenance sleeve which further defines an outlet passage establishing fluid communication between the diluent syringe and the slit valve of the reciprocable stopper.

The lyophilization, mixing, and delivery system of the present invention is preferably configured so that the entire arrangement can be used once and disposed of economically.

Other features and advantages of the present drug packaging, mixing, and delivery system will be become readily apparent from the following detailed description, the accompanying drawings, and the appended claims.

BRIEF DESCRIPTION OF THE DRAWINGS

FIG. 7 is a cross-section view of a preferred embodiment of the syringe system showing a vented primary syringe barrel containing a drug solution with a reciprocable stopper assembly including a sterility maintenance sleeve and a removable plug in a first venting position prior to lyophilization;

FIG. 8 is a cross-section view of the preferred embodiment of the drug-containing primary syringe barrel shown in FIG. 7, and FIG. 8 shows the dry drug after lyophilization with the reciprocable stopper assembly moved to a second sealing position by vacuum and mechanical force;

FIG. 9 is a cross-sectional view of the lyophilized drug-containing primary syringe barrel of the preferred embodiment shown in FIG. 8 with the plug removed from the reciprocable stopper and sterility maintenance sleeve assembly;

FIG. 10 is a cross-sectional view of the preferred embodiment of the primary syringe barrel taken generally along plane 10—10 of FIG. 9;

FIG. 11 is a cross-sectional view of a second diluent syringe barrel connected to the reciprocable stopper assembly of the lyophilized drug-containing primary syringe barrel illustrated in FIG. 9, and FIG. 11 shows the liquid diluent being caused to flow through a one-way valve in the reciprocable stopper and into the mixing chamber of the primary syringe barrel;

DETAILED DESCRIPTION

While the present invention is susceptible of embodiment in various forms, there are shown in the drawings and will hereinafter be described various embodiments, with the understanding the present disclosure is to be considered as an exemplification of the invention, and is not intended to limit the invention to the specific embodiments illustrated.

Figure 1:
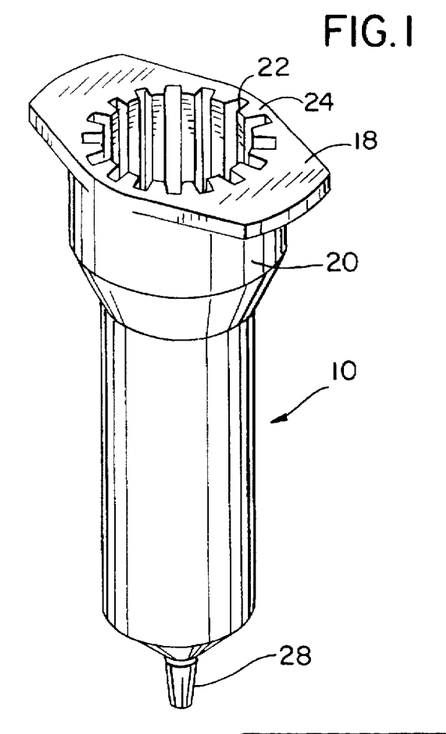
FIG. 1 is a perspective view illustrating a first or primary syringe barrel having an enlarged diameter venting portion with longitudinal channels according to the present invention.
Figure 2:
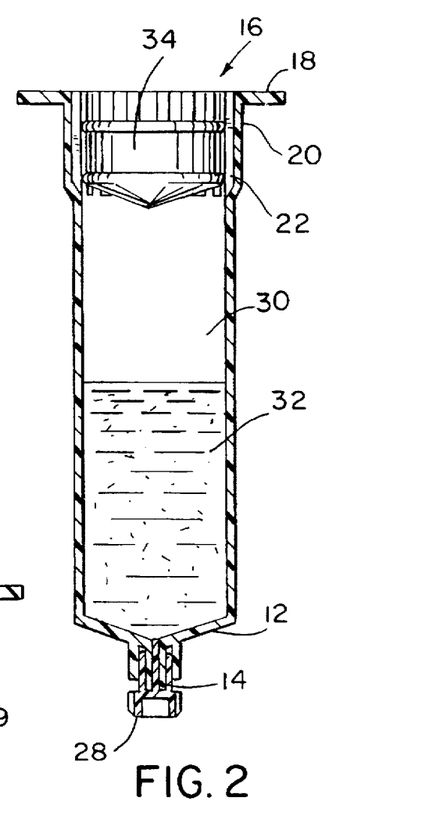
FIG. 2 is a partial cross-sectional view showing a liquid solution in a first syringe barrel with a reciprocable stopper in a first venting position prior to lyophilization.

With reference first to FIGS. 1 and 2, therein is illustrated a first primary syringe barrel 10 embodying the principles of one aspect of the present invention. The primary syringe barrel 10 includes a substantially closed end 12 which defines a delivery passage 14, such as a male luer connection. An open end 16 is opposite the closed end of the primary syringe barrel. The open end 16 typically includes a transverse flange 18. An enlarged diameter portion 20 at the open end 16 of the primary syringe barrel functions as a venting portion and includes at least one channel 22, and preferably a plurality of longitudinal channels 22, on the interior surface 19 of the first syringe barrel. The channels 22 define rib portions 24 between the channels. Alternatively, as shown in FIG. 14, raised rib portions 124A on the enlarged diameter portion of the primary syringe barrel define the channels 122A. The interior surfaces of the rib portions 24 and raised rib portions 124A lie on a circular locus having generally the same diameter as the interior surface 19 or 118 respectively of the remainder of the primary syringe barrel 10 or 10A.

A removable closure 28 having a longitudinal stem 29 is provided for sealing the delivery passage 14 of the primary syringe barrel 10 to define a first or mixing chamber 30. The mixing chamber 30 is filled with a predetermined volume of a medical solution 32 of a predetermined drug concentration. A resilient reciprocable stopper 34 is positioned in the venting portion 20 of the barrel 10 as shown in FIG. 2. The reciprocable stopper 34 may also be described as a slidable piston or a grommet or a slidable seal, and these terms may be used interchangeably.

The liquid solution 32 in the first primary syringe barrel is then subjected to a lyophilization procedure. Briefly, the lyophilization procedure includes sealing the syringe barrel 10 in a lyophilization chamber (not illustrated). The lyophilization chamber is then rapidly reduced in temperature so that the liquid in the drug solution freezes. The lyophilization chamber is then subjected to vacuum, and heat energy is supplied to the frozen liquid to provide energy for sublimation so that the frozen liquid is converted directly to a vapor. The longitudinal channels 22 in the primary syringe barrel permit the vapor to be evacuated from the mixing chamber 30 of the primary syringe barrel 10 leaving only a powder form or dry drug concentrate 40.

Figure 3:
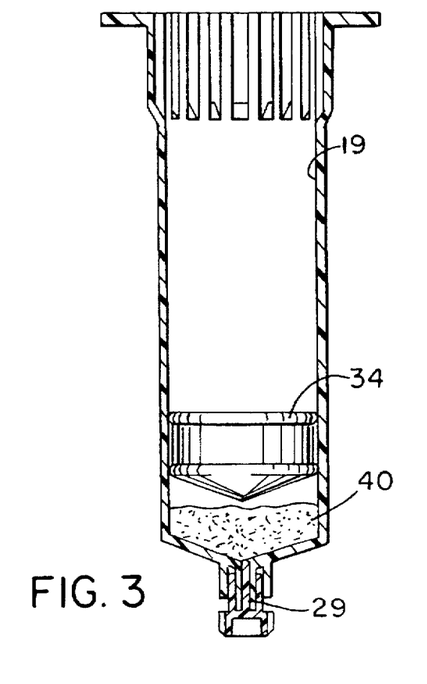
FIG. 3 is a cross-sectional view of the first syringe barrel after lyophilization showing the resultant drug powder and the reciprocable stopper in the second, sealing position.

After lyophilization, only the reduced volume of drug in powder form 40 that results from the lyophilized solution remains in the first syringe barrel 10. The slidable reciprocable stopper 34 is then moved inward from the first position abutting the longitudinal channels 22, as shown in FIG. 2, to sealingly enclose the dry powder 40 in the substantially closed end of the primary syringe barrel 10 as shown in FIG. 3. After the primary syringe barrel 10 is removed from the lyophilization chamber, the primary syringe barrel 10 containing the lyophilized drug 40 can be packaged and sterilized as needed.

To reconstitute the lyophilize drug 40 to a solution state for IV administration from the primary syringe barrel through the delivery passage 14 of the primary syringe barrel, a second, diluent syringe 44 is placed in fluid communication with the dry drug 40 in the primary syringe barrel 10.

Figure 4:
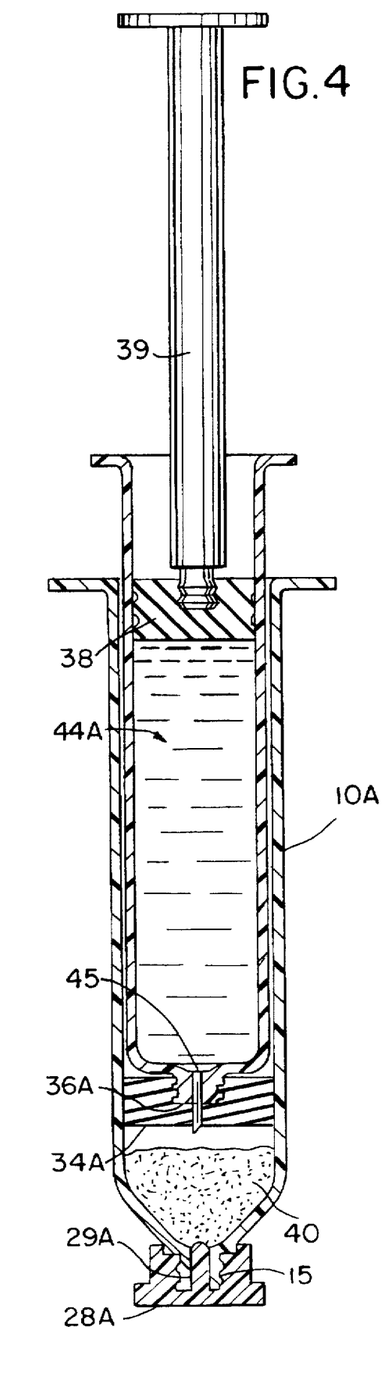
FIG. 4 is a cross-sectional view of an alternative lyophilized drug-containing primary syringe barrel having a second diluent syringe connected by a sharp cannula connection.
Figure 5:
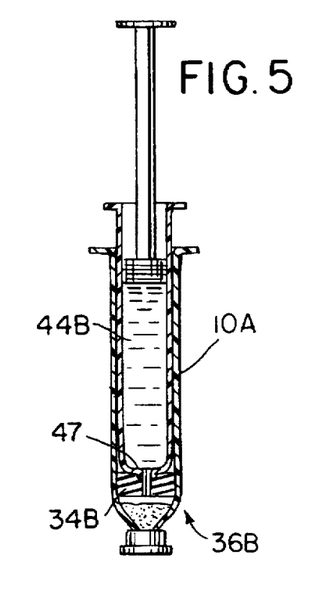
FIG. 5 is a schematic view showing an alternative lyophilized drug-containing primary syringe barrel having a second diluent syringe connected by a one-way valve and valve actuating connector.
Figures 5A, 14:
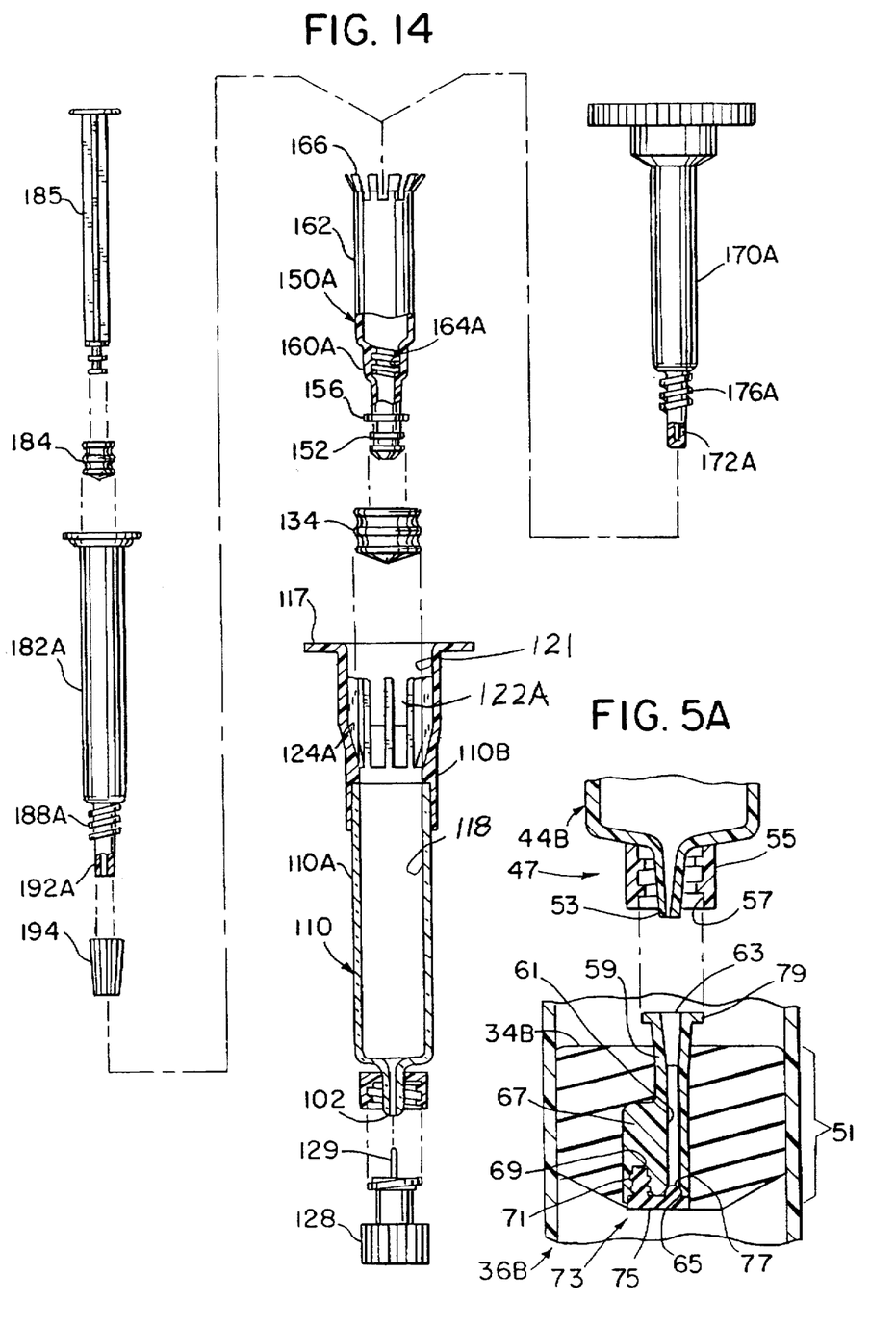
FIG. 5A is an enlarged, fragmentary, cross-sectional view of one form of a one-way valve in the reciprocable stopper and a valve actuating connector.
FIG. 14 is an exploded cross-sectional view of an alternate preferred embodiment showing another primary syringe barrel with a reciprocable stopper and sterility maintenance sleeve assembly, and with a removable plug or alternatively with a second diluent syringe.
Figure 6:
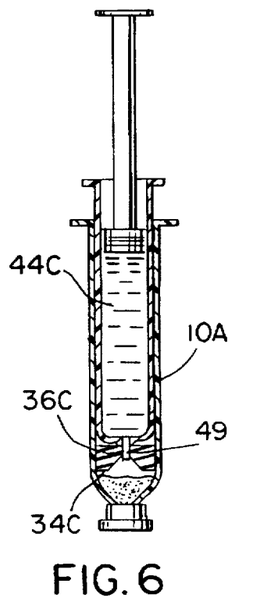
FIG. 6 is a schematic view showing an alternative lyophilized drug-containing primary syringe barrel having a second diluent syringe connected by a blunt cannula and having a prepierced reciprocable stopper.

Referring now to FIGS. 4, 5, and 6, three embodiments of a reciprocable stopper, 34A, 34B, and 34C are depicted in the primary syringe assembly for fluid communication with an appropriate diluent syringe. Although not shown in FIGS. 4–6, each primary syringe barrel 10A may have, at the upper open end, an enlarged diameter venting portion with ribs defining channels as described above with reference to FIGS. 1–3 to permit prior lyophilization of the drug solution in the primary syringe barrel. The first primary syringe barrel 10A in FIGS. 4–6 is also shown as having a male thread configuration at the delivery end passage 15 and a removable closure 28A that differs from the embodiment described with respect to FIGS. 1–3.

In FIG. 4, the reciprocable stopper 34A is similar to a conventional resealable elastomeric stopper, in that the stopper can be penetrated by a sharp cannula 45 on the diluent syringe 44A. The second diluent syringe 44A includes a movable piston plunger 38 and plunger stem 39. Provision is also made for attachment, such as by threads 36A, of the diluent syringe hub to the reciprocable stopper 34A.

In FIG. 5, the reciprocable stopper 34B is schematically represented as including a one-way valve 36B such as, for example, a flapper valve or other type of pressure actuable valve commonly used in medical technology. The diluent syringe 44B is schematically shown as including a valve actuating connector 47, such as a male luer connector.

As illustrated in FIG. 5A a reciprocable stopper 34B is sealingly and slidably disposed in a first syringe barrel 10A, and a valve assembly 51 is mounted in the reciprocable stopper 34B for fluid communication engagement by a second syringe barrel 44B. The bottom end of the second syringe barrel 44B includes an outwardly projecting discharge nozzle 53 in the form of a male luer nozzle which defines a discharge passage. The luer nozzle 53 is surrounded by an annular collar 55 which defines a female thread form 57. A movable piston plunger (not Illustrated but similar to the movable piston plunger 38 shown in FIG. 4) is disposed in the second syringe barrel 44B.

The valve assembly 51 includes a generally elongate conduit 59 that extends through the reciprocable stopper 34B and that defines an internal flow passage 61 having an inlet 63 and an outlet 65.

The valve assembly 51 includes a laterally projecting boss 67 defining a receiving cavity 69 for receiving a ribbed anchor portion 71 of a valve member insert 73. The valve member insert 73 includes a transversely oriented, resilient, spring member 75 extending from the lower end of the anchor portion 71. A frusto-conical, flapper valve portion 77 projects upwardly from the spring member 75. The interior surface of the valve portion 77 is adapted to seal against the conduit outlet 65. The spring member 75 normally biases the valve portion 77 in tight sealing engagement against the conduit outlet end 65 as illustrated in FIG. 5A. The above construction defines one example of a one-way flow valve in the reciprocable stopper 34B.

The inlet end of the valve assembly 51 includes a connector which may be a flange 79 or male thread form, such as is employed in luer connection systems marketed under the trademark LUER-LOK. This accommodates connection of the reciprocable stopper 34B to the second diluent syringe barrel 44B. In particular, the second barrel collar 55 can be threadingly engaged with the thread form or flange 79 at the inlet end of the valve assembly 51 projecting from the reciprocable stopper 34B in the first syringe barrel 10A The second barrel discharge nozzle 53 is adapted to enter into the inlet 63 of the valve assembly 51 and form a leak-tight seal with the conduit 59. After inserting the second syringe barrel 44B to engage the collar 55 with the flange 79, the connection process is completed by effecting relative rotation between the two syringe barrels 10A and 44B to complete the threaded engagement. The second syringe barrel nozzle 53, collar 55, and valve assembly 51 thus function as a cooperating fluid transfer connector means or fluid communicating and connecting means for fluidly communicating the liquid diluent in the second syringe barrel 44B through the reciprocable stopper 34B to the dry drug 40 in the mixing chamber of the primary syringe barrel 10A. Other suitable connection structures could be used in place of the specific form of the nozzle 53, collar 55, and valve assembly 51 illustrated.

Preferably, a secondary, removable closure member (not illustrated but which may be in the form of a threaded plug) is threadingly engaged with the collar 55 to seal discharge nozzle 53. The closure must be removed prior to use of the second diluent syringe.

Subsequently, the movable piston plunger 38 of the second syringe barrel can be pushed into the second syringe barrel 44B to force the liquid second constituent or liquid diluent past the valve portion 77 into the first primary syringe barrel 10A to mix with the dry drug 40. As this occurs, the reciprocable stopper 34B and second barrel 44B are forced relatively outwardly by the hydraulic pressure of the liquid diluent in the mixing chamber 30 and toward the open end 16 of the primary syringe barrel.

Alternatively, or concurrently, the second syringe barrel 44B can be moved (i.e., drawn or pulled) outwardly relative to the first syringe barrel 10A. As the second syringe barrel 44B and attached reciprocable stopper 34B are moved outward relative to and within the first primary syringe barrel 10A, the volume in the mixing chamber 30 beneath the reciprocable stopper 34B increases and thus lowers the pressure within the mixing chamber. The pressure differential can open the valve portion 77 so that the liquid second constituent or liquid diluent flows into the first syringe barrel 10A to combine with the dry drug 40. Ambient air pressure acting on the exterior surface of the movable piston plunger 38 of the second syringe barrel is also transferred to the liquid diluent.

The two syringe barrels 10A and 44B move oppositely until the bottom surface of the movable piston plunger 38 of the second syringe barrel 44B contacts the bottom, interior surface of the second syringe barrel.

At this point, all of the liquid diluent has been expelled from the second syringe barrel 44B into the first primary syringe barrel 10A. The primary syringe assembly can then be shaken to ensure good mixing.

The first syringe barrel 10A would typically have a delivery end removable closure 28A (shown in FIG. 4). Such a removable closure would be removed to permit administration of the mixed drug solution in the primary syringe barrel 10A to a patient. The administration is effected by pushing the second syringe barrel 44B (along with the stem portion 39 of the movable piston plunger 38) inward relative to the first syringe barrel 10A to move the reciprocable stopper 34B further into the first primary syringe barrel 10A to expel the mixed drug contents.

In FIG. 6, a reciprocable stopper 34C is illustrated as including a thin membrane or prepierced elastomeric reseal 36C. The diluent syringe 44C includes a blunt cannula connector 49, and can be similarly operated as described above.

Any of the above described diluent syringes 44A, 44B, and 44C and fluid flow connectors 45, 47, and 49 are usable with the primary syringe barrel of the present invention that was vented for lyophilization as previously described herein with respect to FIGS. 1-3.

Another embodiment of the invention, in a presently preferred form, is illustrated in FIGS. 7-14. The preferred embodiment is a syringe system for accommodating lyophilization of a liquid drug, storing the lyophilized drug, separately storing a diluent, combining the lyophilized drug and diluent to reconstitute the lyophilized drug to solution form, and administration of the drug solution from a primary syringe barrel.

The system includes a first or primary syringe barrel 110. The first syringe barrel 110 includes a substantially closed end 112 which defines a delivery passage 114. The delivery passage preferably includes a male luer connection nozzle 102 surrounded by an annular collar 104 defining an interior, female thread 106.

The delivery passage 114 is preferably closed with a removable closure 128 which has an internal stem 129 for occluding the delivery passage 114. The removable closure 128 also preferably includes an exterior lug or flange 108 for threadingly engaging the female thread 106 on the annular collar 104 at the delivery end of the first syringe barrel 110.

The first syringe barrel 110 has an opposite open end 116 with a transverse flange 117. The first syringe barrel 110 is preferably cylindrical and preferably has a cylindrical interior surface 118. The syringe barrel 110, adjacent the open end 116, has an enlarged diameter portion or venting portion 120 (FIG. 7) which defines at least one longitudinal channel 122. Preferably, there are a plurality of longitudinal channels 122 in the venting portion of the syringe barrel 110. The channels 122 define rib portions 124 between the channels 122.

Alternatively, as shown for example in FIG. 14, the primary syringe barrel 110 may be constructed as two pieces. A front barrel portion 110A is joined to a rear barrel portion 110B. The front barrel portion 110A may be glass while the rear barrel portion 110B may be a molded plastic part. Also in either the one piece primary syringe barrel 110 or the two piece primary syringe barrel construction, as shown in FIG. 14, raised rib portions 124A on the enlarged diameter portion 120 may define the channels 122A therebetween. In any configuration, the interior surfaces of the rib portions 124 or 124A lie in a circular locus that has the same diameter as the interior surface 118 of the primary syringe barrel below the channels 122. An enlarged diameter portion 121 without ribs or channels is defined above the venting portion 120.

When the removable closure 128 is properly secured to the first syringe barrel 110, the primary syringe barrel 110 functions as a container defining a first or mixing chamber 130 which can be filled with a predetermined quantity of a medical solution or liquid drug 132 which has a predetermined drug concentration.

A reciprocable stopper 134 is disposed within the first syringe barrel 110 at a first position adjacent the channels 122. The reciprocable stopper 134 may also be described as a slidable piston or a grommet or a slidable seal, and these terms may be used interchangeably.

The reciprocable stopper 134 has an outer side 135 facing the first syringe barrel open end 116 and has an inner side 137 facing the first syringe barrel delivery passage 114. The length of the reciprocable stopper 134 is shorter than the length of the channels 122.

Figure 11:
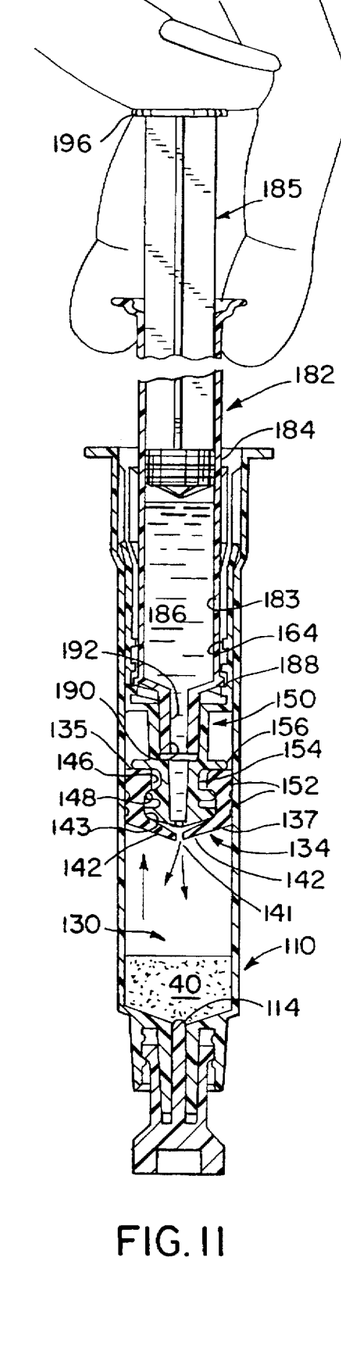

As best illustrated in FIG. 11, the reciprocable stopper 134 has a resilient central portion which is preferably hollow and which has at least one longitudinal slit 141 defining resilient lips 142 which are biased to a normally closed position. The resilient lips 142 can open at the inner side 137 of the reciprocable stopper 134 toward the first syringe barrel delivery passage 114 when pressurized from the outer side 135 of the reciprocable stopper (such as by hydraulic pressure from a second diluent syringe assembly described hereinafter.) Preferably, the inner side 137 of the reciprocable stopper defines a generally conical surface when the slit 141 and resilient lips 142 are closed.

The reciprocable stopper 134 has an enlarged receiving cavity 143 defined in the central portion of the reciprocable stopper adjacent the resilient lips 142. The reciprocable stopper 134 has a smaller entrance passage 146 between the outer side 135 of the reciprocable stopper and the enlarged receiving cavity 143 so as to define a retention shoulder 148 around the smaller entrance passage 146.

With continued reference to FIG. 11, the reciprocable stopper 134 is adapted to be mounted to the end of a sterility maintenance sleeve 150. The sterility maintenance sleeve 150 has an outlet end defining an enlarged head 152 which is force-fit into the enlarged receiving cavity 143 of the resilient reciprocable stopper 134. The sterility maintenance sleeve 150 includes a reduced diameter neck 154 which is received in the smaller entrance passage 146 of the reciprocable stopper 134. A support flange 156 projects radially outwardly from the top of the neck 154 of the sterility maintenance sleeve adjacent the reciprocable stopper outer side 135. The flange 156 functions as a support which keeps the reciprocable stopper 134 from collapsing or otherwise excessively deforming in a way that would permit undesirable fluid leakage from the primary syringe barrel 110.

Figures 7, 8, 9, 10:
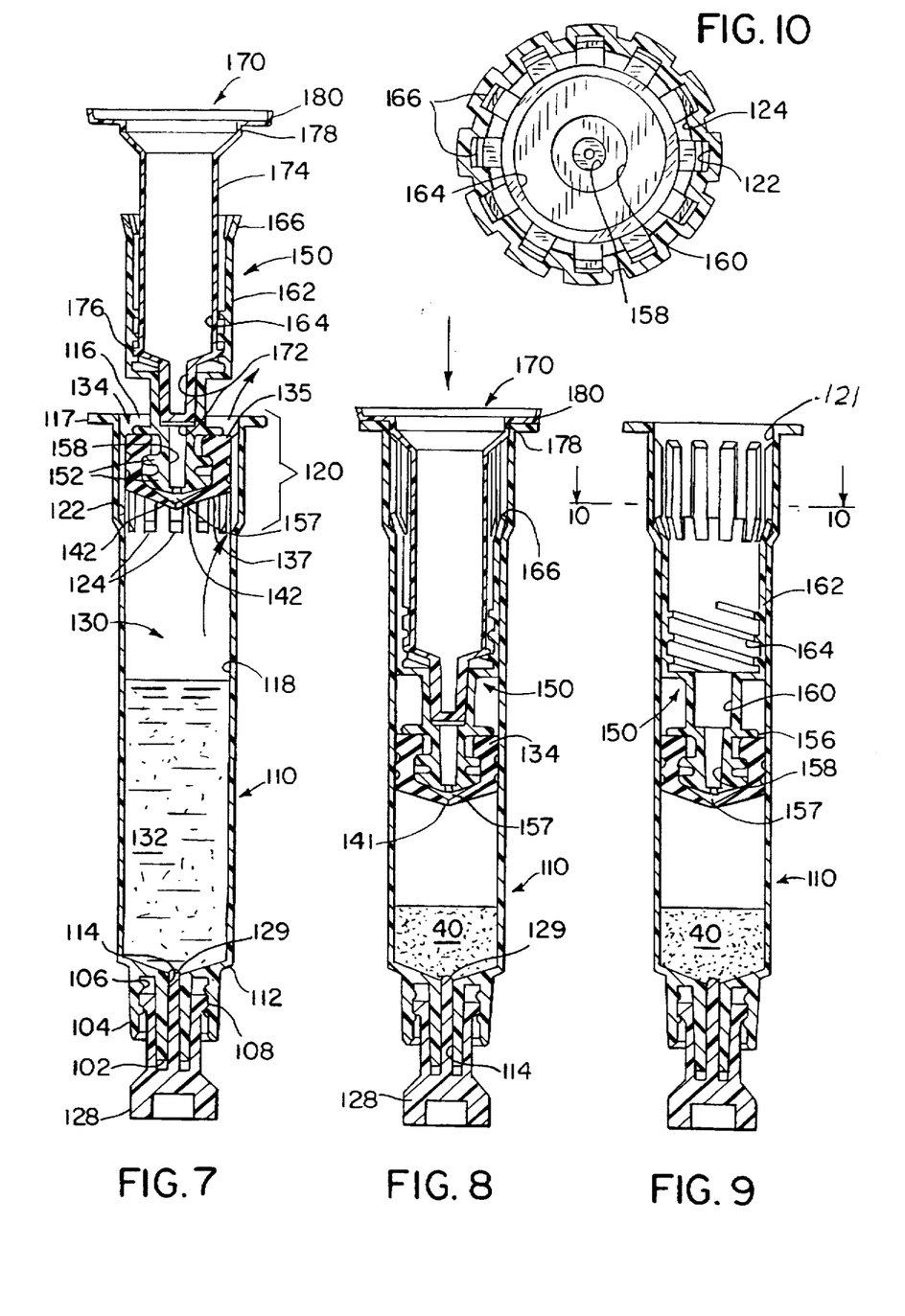

As illustrated in FIG. 7, the reciprocable stopper 134 preferably defines a clearance space 157 or clearance chamber between the resilient lips 142 of the reciprocable stopper and the bottom distal surface of the enlarged head 152 at the outlet end of the sterility maintenance sleeve 150. The clearance space 157 insures that the resilient lips 142 will always be able to close tightly in the absence of a pressure differential sufficient to open them as described in detail hereinafter.

The outlet end of the sterility maintenance sleeve 150 defines an outlet passage 158 from which fluid can flow into the clearance space 157 between the sterility maintenance sleeve outlet end and the resilient lips 142 of the reciprocable stopper 134. As illustrated in FIG. 9, the upper end of the sterility maintenance sleeve outlet passage 158 communicates with the interior of a female luer socket 160 which projects upwardly through and above the support flange 156 of the sterility maintenance sleeve. The luer socket 160 is adapted to receive a luer nozzle of a diluent syringe as explained in detail hereinafter.

With continued reference to FIG. 9, the sterility maintenance sleeve 150 has a large diameter body portion 162 having an interior female thread 164. As illustrated in FIG. 7, the upper end of the sterility maintenance sleeve body portion 162 has at least one deflectable, anti-rotation tab 166 or flexible tab which projects outwardly. Preferably, as illustrated in FIG. 10, there are a plurality of spaced-apart anti-rotation tabs 166 oriented in a circular locus at the top of the large diameter body portion 162 of the sterility maintenance sleeve.

As illustrated in FIG. 7, a removable plug 170 is provided for being initially inserted into and sealing the interior of the sterility maintenance sleeve 150. The plug 170 includes a nozzle-shaped distal end 172 for sealing the outlet passage 158 and luer socket 160 of the sterility maintenance sleeve 150. The distal end 172 of the plug is closed and therefore does not allow any fluid communication into the outlet passage 158 of the sterility maintenance sleeve. The distal end 172 of the plug seals the interior of the mixing chamber 130 from the outside environment.

The removable plug 170 also includes a cylindrical body portion 174 which has, at its lower end, an exterior engaging member 176 for threadingly engaging the interior, female thread 164 on the large diameter body portion 162 of the sterility maintenance sleeve 150. The upper end of the plug 170 includes an exterior seal wall 178 for sealing the sterile interior of the primary syringe barrel 110 and the sterility maintenance sleeve 150 as described in detail hereinafter.

Alternatively, as shown in the exploded view of FIG. 14, a modified sterility maintenance sleeve 150A has a large diameter body portion 162 but the interior female thread form 164A is on an extending portion of the narrower luer socket 160A. The removable plug 170A of FIG. 14 includes a male thread form 176A on the extended nozzle-shaped distal end 172A. The distal end 172A of the plug seals the interior of the mixing chamber 130 from the outside environment.

The removable plug 170 also includes a graspable portion 180. Preferably, the graspable portion 180 has an enlarged cross section and has an exterior surface which can be easily grasped to rotate the plug 170 to unthread it from the sterility maintenance sleeve 150 as described in detail hereinafter.

Figure 11A:
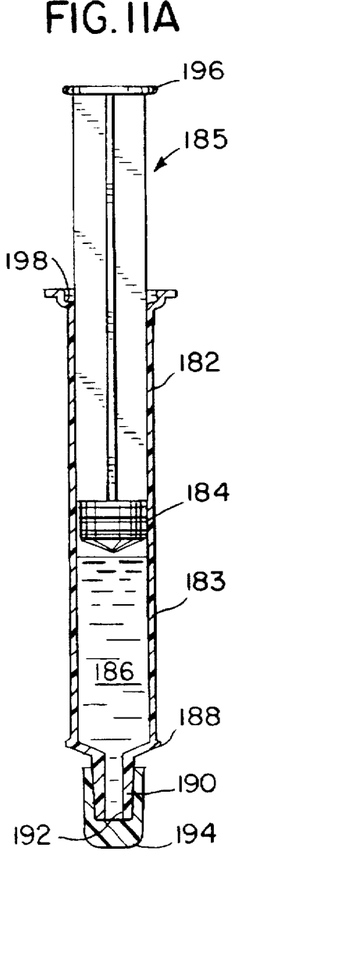
FIG. 11A is a cross-sectional view of the second, diluent syringe assembly shown in FIG. 11.

The preferred embodiment of the syringe system also includes a second or diluent syringe 182 as illustrated in FIG. 11A. The diluent syringe 182 includes a diluent syringe barrel 183 that holds a liquid diluent 186. The lower portion of the diluent syringe barrel 183 has an exterior engaging member 188 for engaging the interior female thread 164 of the sterility maintenance sleeve 150 as described in detail hereinafter. The diluent syringe barrel 183 has a discharge end 190 in the form of a luer nozzle 192 defining a discharge passage. Preferably, a removable closure 194 is provided for sealingly closing the discharge passage 192 of the diluent syringe. The removable closure 194 may employ a friction fit. Alternatively, the removable closure may employ a snap-fit or a threaded connection.

In an alternative preferred embodiment shown in FIG. 14, a modified second diluent syringe 182A includes an extended portion 192A of the narrower luer nozzle 192 at the lower portion of the diluent syringe barrel 183. The narrow extension 192A includes a male thread form 188A for engagement with the narrower interior female thread 164A on the modified sterility maintenance sleeve 150A.

In either embodiment, the diluent syringe assembly 182 or 182A also includes a movable piston plunger 184 and a plunger stem 185. The movable piston plunger 184 is preferably elastomeric and is movably and sealingly disposed in the diluent syringe barrel 183. The movable piston plunger 184 is used to express the liquid diluent 186 out of the diluent syringe barrel 183 through the discharge passage luer nozzle 192 when the luer nozzle Is sealingly positioned in the luer socket 160 of the sterility maintenance sleeve of the primary syringe barrel 110.

The preferred embodiment of the syringe system may be provided to the user as a package of two separate subassemblies. One subassembly includes the filled and capped diluent syringe barrel 183 as illustrated in FIG. 11A for example. The other subassembly includes the primary syringe barrel 110 containing a lyophilized drug 40 with the remaining components fitted together and sealed by the removable closure 128 and removable plug 170 as illustrated in FIG. 8.

The syringe system of the present invention accommodates lyophilization of a liquid drug by the manufacturer when a drug solution 132 is initially provided in the first syringe barrel 110. For this purpose, the manufacturer initially assembles the primary syringe components in a first orientation as shown in FIG. 7. The primary syringe barrel 110 is then filled with a predetermined quantity of a medical or liquid drug solution 132 having a predetermined drug concentration. The reciprocable stopper 134, including the attached sterility maintenance sleeve 150 which is sealed by the removable plug 170, is initially located in the primary syringe barrel 110 adjacent the venting channels 122 at a first position (FIG. 7). The first venting position of the reciprocable stopper permits passage of vapor around the reciprocable stopper 134 through the venting channels 122. Venting permits the solution in the primary syringe barrel 110 to be lyophilized as previously described.

The lyophilization procedure includes enclosing the primary syringe barrel 110 in a sealed lyophilization chamber (not illustrated). The lyophilization chamber is then rapidly reduced in temperature so that the liquid drug solution 132 freezes. The lyophilization chamber is then subjected to vacuum, and heat energy is supplied to the frozen liquid to provide energy for sublimation so that the frozen liquid is converted directly to a vapor. The vapor is drawn off through the longitudinal channels 122 in the primary syringe barrel 110 to leave only a powder form or dry drug concentrate 40 of the lyophilized drug (FIG. 8).

As shown in FIG. 8, after lyophilization the removable plug 170 is pushed downward to move the sterility maintenance sleeve 150 and the reciprocable stopper 134 downward together to a second, sealing, storage position. Preferably, mechanical forces are applied to the plug 170 as well as the vacuum which is also drawn on the sealed reciprocable stopper assembly 134. The exterior seal wall 178 of the plug seals on the enlarged diameter interior 121 of the first syringe barrel 110 above the upper ends of the channels 122 and ribs 124.

As the sterility maintenance sleeve 150 moves downward, the outwardly projecting anti-rotation tabs 166 on the upper end of the sterility maintenance sleeve 150 are received in the channels 122 of the first syringe barrel 110. If necessary, the components can be rotated slightly to insure proper engagement of the flexible tabs 166 in the channels 122. The enlarged graspable portion 180 of the plug abuts the end of the primary syringe barrel 110 as shown in FIG. 8. The enlarged portion 180 limits the extent of the insertion of the assembled reciprocable stopper 134, plug 170, and sterility maintenance sleeve 150 in the primary syringe barrel 110, when the components are in the storage orientation illustrated in FIG. 8. The lyophilized dry drug 40 does not occlude the first syringe delivery passage 114 because the delivery passage 114 is occluded by the inwardly projecting stem 129 on the removable closure 128.

The primary syringe 110 subassembly illustrated in FIG. 8 and the diluent syringe 182 subassembly illustrated in FIG. 11A can be provided to the user in a single package or as two separate packages which can be stored for later use. At the time of use, the removable plug 170 is removed from the sterility maintenance sleeve 150 of the fist syringe barrel 110 by rotating the plug in the counterclockwise (or clockwise) direction to unthread the plug 170 from the sterility maintenance sleeve 150. The flexible tabs 166 of the sterility maintenance sleeve remain engaged with the channels 122 and prevent the sterility maintenance sleeve 150 from rotating relative to the primary syringe barrel 110. This permits the removable plug 170 to be readily unscrewed from the sterility maintenance sleeve 150. Preferably, the graspable portion 180 of the plug 170 has a knurled surface to accommodate the grasping of the end portion 180 between the thumb and fingers of a healthcare user.

Next, the diluent syringe 182 (FIG. 11A) is prepared for insertion into the sterility maintenance sleeve 150. The diluent syringe 182 can be inverted and the removable closure 194 removed. The first syringe barrel 110 can also be inverted and aligned with the inverted diluent syringe barrel 183. Relative longitudinal movement can then be effected so as to telescopically insert the diluent syringe barrel 183 into the sterility maintenance sleeve 150 in the primary syringe barrel 110. The exterior engaging member 188 on the diluent syringe barrel 183 is threadingly engaged with the interior female thread 164 of the sterility maintenance sleeve as shown in FIG. 11. The diluent syringe barrel 183 is screwed into the sterility maintenance sleeve 150 until it reaches the fully threaded and sealed position illustrated in FIG. 11.

Alternatively, as shown in FIG. 14, the diluent syringe barrel 183A is configured similarly but with the male thread form 188A on the extended portion of the narrower luer nozzle 192A. The male thread form 188A is thus engaged with the female thread form 164A in the sterility maintenance sleeve 150A of the primary syringe barrel 110.

Figure 12:
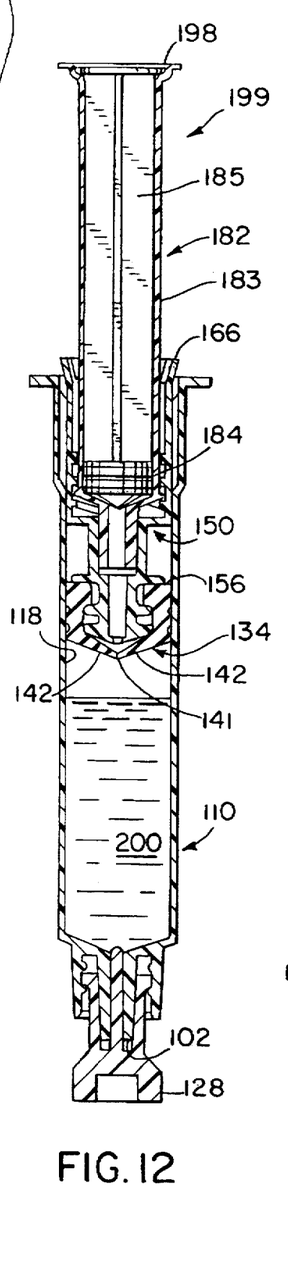
FIG. 12 is a cross-sectional view similar to FIG. 11, but FIG. 12 shows the empty diluent syringe barrel with the plunger stem locked to the second syringe barrel and with the mixed constituents in the mixing chamber of the primary syringe barrel.

Referring now to FIGS. 11 and 12, the liquid diluent 186 in the diluent syringe barrel 183 is expressed into the primary syringe barrel 110. This is achieved by pushing the plunger stem 185 inward relative to the diluent syringe barrel 183.

The slit 141 in the reciprocable stopper 134 opens under the increased pressure resulting from the movement of the movable piston plunger 184. The liquid diluent 186 is thus forced into the mixing chamber 130 of the primary syringe barrel 110 as shown in FIG. 11. The liquid diluent 186 is thus combined with the lyophilized drug 40 for reconstituting the drug in solution form 200. As the liquid diluent 186 fills the mixing chamber 130 in the primary syringe barrel 110, the reciprocable stopper 134 is forced to slide outwardly in the primary syringe barrel 110, and the volume of the mixing chamber 130 increases. As the reciprocable stopper 134 slides outwardly, the sterility maintenance sleeve 150 and diluent syringe barrel 183 move outwardly with the reciprocable stopper 134.

Instead of solely pushing the plunger stem 185 inward relative to the diluent syringe barrel 183 to force the liquid diluent 186 into the first primary syringe barrel 110, the user may, alternatively, or concurrently pull or draw the diluent syringe barrel 183 outward relative to the primary syringe barrel 110. Pulling the diluent syringe barrel will create a pressure differential as the mixing chamber 130 expands which will then cause the liquid diluent 186 to flow into the lower pressure mixing chamber 130.

The sterility maintenance sleeve 150 maintains the sterility of the interior surface 118 of the primary syringe barrel 110 before and during the outward movement of the reciprocable stopper 134 with the primary syringe barrel 110. When the liquid diluent 186 is discharged from the diluent syringe barrel 183 into the expanding mixing chamber 130 of the primary syringe barrel 110, the sterile dry drug 40 and the sterile liquid diluent 186 are mixing in an expanding and uncontaminated mixing chamber 130.

As shown in FIG. 12, the upper end of the sterility maintenance sleeve 150 eventually moves outwardly far enough so that the flexible tabs 166 clear the open end 116 of the first syringe barrel 110. Also, when all of the liquid diluent 186 has been expressed from the diluent syringe assembly 182, the movable piston plunger 184 bottoms out in the diluent syringe barrel 183. Preferably, the upper, distal end of the plunger stem 185 of the diluent syringe has a radial flange 196, and the upper, distal end of the diluent syringe barrel 183 has a snap-fit type groove 198. The snap-fit groove 198 receives and holds the radial flange 196 of the plunger stem in a snap-fit engagement. The snap-fit groove and radial flange retains the plunger stem 185 and second syringe barrel 183 in a snapped-together condition 199. This prevents the plunger stem 185 from being drawn outward from the diluent syringe barrel 183 once the liquid diluent has been delivered from the diluent syringe assembly 182.

Figure 13:
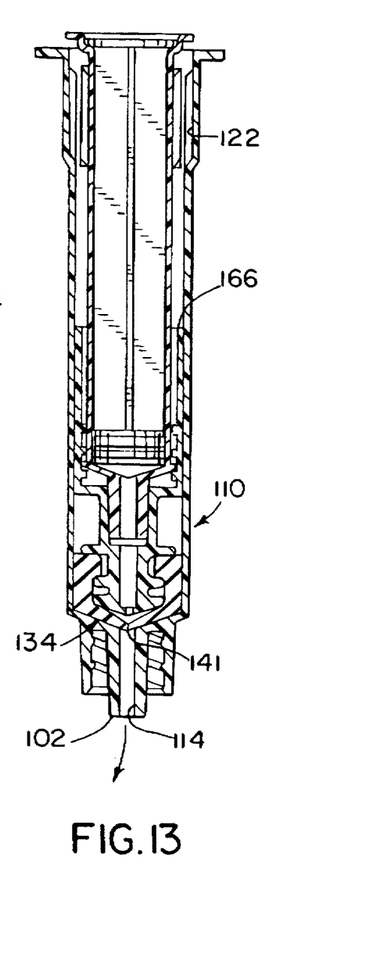
FIG. 13 is a cross-sectional view similar to FIG. 12, but FIG. 13 shows the first syringe barrel with the snapped-together second syringe assembly and reciprocable stopper assembly moved toward the delivery passage of the primary syringe barrel to cause the mixed constituents to flow from the primary syringe barrel.

The snapped-together diluent syringe assembly, now designated 199 in FIG. 12, can now function, in conjunction with the sterility maintenance sleeve 150 and reciprocable stopper 134 which are attached thereto, as the plunger for the primary syringe barrel 110. In order to dispense the reconstituted liquid drug 200, the primary syringe assembly shown in FIG. 12 can first be shaken to insure good mixing and then inverted. The closure 128 is then removed from the inverted assembly. The snapped-together diluent syringe assembly 199 (i.e. syringe barrel 183 and plunger stem 185) is then pushed to remove air from or prime, the primary syringe barrel 110. The nozzle 102 of the primary syringe assembly may then be connected to an appropriate IV administration set or other conduit. Then the snapped-together second syringe assembly 199 is pushed further inward in the primary syringe barrel 110 to express the liquid drug 200 out of the primary syringe barrel 110. The back pressure of the liquid drug 200 in the first syringe barrel 110 forces the slit 141 in the reciprocable stopper 134 to close (if the resilient lips 142 have not already closed) and to remain closed. The support flange 156 on the sterility maintenance sleeve prevents undue deformation of the reciprocable stopper 134. This support prevents leakage around the reciprocable stopper 134 between the reciprocable stopper and the interior surface 118 of the first syringe barrel 110. Further, the clearance space 157 between the enlarged head at the lower end of the sterility maintenance sleeve 150 and the inside of the reciprocable stopper lips 142 permits the resilient lips 142 on each side of the slit 141 to fully close.

As the snapped-together syringe assembly 199 is pushed further inward into the primary syringe barrel 110, the deflectable tabs 166 on the upper end of the sterility maintenance sleeve 150 are deflected inward at the lower ends of the channels 122 so that the sterility maintenance sleeve 150 can move completely past the channels 122 as the reciprocable stopper 134 moves to the bottom end of the first primary syringe barrel 110.

Use of the syringe system of the present invention for IV drug administration promotes efficient and effective lyophilization, packaging, reconstitution, and delivery of a lyophilized drug from a single syringe system without transfer from another intermediate mixing container. The above described system thus reduces or eliminates the time for preparation, the chance of contamination, and most disposable medical by-products other than the syringe system itself. At most, only ancillary packaging components such as the removable closures and the removable plug for the syringe, plus any overwrap for the system, will need to be disposed.

From the foregoing, it will be observed that numerous modifications and variations can be effected without departing from the true spirit and scope of the novel concept of the present invention. The present disclosure is to be understood broadly and no limitation with respect to the specific embodiments herein is intended or should be inferred. The disclosure is intended to cover, by the appended claims, all such modifications as falls within the scope of the claims.

What is claimed is:

1. A syringe system comprising:

a primary syringe barrel having a delivery end defining a delivery passage and an opposite end having an edge and a venting portion with an inner surface and a larger transverse cross section;

a removable closure sealing the delivery passage of the primary syringe barrel to define a chamber for containing a medical solution;

a plurality of longitudinal channels on the inner surface of the venting portion of the open end of said primary syringe barrel;

a plurality of rib portions in the venting portion between said channels, said opposite end of said primary syringe barrel has a smooth portion along the inner surface between said edge and said rib portions; and a reciprocable stopper for slidably sealing said primary barrel wherein the reciprocable stopper has a first position abutting the channels of the inner surface of the venting portion to allow the medical solution to be lyophilized, and is then axially movable in the direction of the delivery passage to a second position to sealingly enclose the lyophilized drug within the sealed delivery end of the primary syringe barrel.

2. The syringe system of claim 1 wherein said reciprocable stopper further includes fluid transfer connector means for fluid communication through said reciprocable stopper from the direction of the open end of the primary syringe barrel.

3. The syringe system of claim 2 wherein said fluid transfer connector means includes (1) a portion of said reciprocable stopper that is penetrable, and (2) an associated penetrating means for penetrating said reciprocable stopper.

4. The syringe system of claim 3 wherein said penetratable portion of said reciprocable stopper is a prepierced elastomeric portion configured to allow fluid transfer only in the direction toward the discharge end of the primary syringe barrel.

5. The syringe system of claim 4 wherein said associated penetrating means is a blunt cannula.

6. The syringe system of claim 2 wherein said fluid transfer connector means includes a one way valve; and a valve actuating flow connector.

7. The syringe system of claim 3 wherein said penetratable portion of said reciprocable stopper is a resealable elastomeric portion.

8. The syringe system of claim 7 wherein said associated penetrating means is a sharp cannula.

9. The syringe system of claim 1 wherein said primary syringe barrel has an interior surface adjacent said delivery end; and said venting portion has a larger transverse cross section than said interior surface; and said venting portion has a larger transverse cross section than said interior surface; and said syringe system further comprising a fluid transfer connector means including a resilient central portion in said reciprocable stopper which has at least one slit defining resilient lips which are biased to a normally closed position and which can open toward the delivery passage of said first syringe barrel.

10. The syringe system of claim 1 wherein the reciprocable stopper has a body and proximal sealing ring with a larger diameter than the body of said stopper to act as a positioning stop against said rib portions.

11. A syringe system for accommodating lyophilization of a liquid drug, storing the lyophilized drug, separately storing a diluent, combining the lyophilized drug and diluent to reconstitute the lyophilized drug to solution form for administration, and dispensing the solution, said system comprising:

a first syringe barrel for initially containing a liquid drug and having (1) a delivery end defining a delivery passage, (2) an opposite open end, (3) an interior surface, and (4) a venting portion including at least one longitudinal channel in said venting portion;

a removable closure sealing closed said delivery passage;

a reciprocable stopper that has (1) an outer side facing said first syringe barrel open end, and (2) an inner side facing said first syringe barrel delivery passage, said reciprocable stopper being initially locatable in said first syringe barrel adjacent said longitudinal channel at a first position which permits passage of vapor around said reciprocable stopper through said channel out of said first syringe barrel during lyophilization, said reciprocable stopper subsequently being movable to positions inward of said channel of the venting portion wherein said interior surface is sealingly engaged for sealing the lyophilized drug in said first syringe barrel;

a sterility maintenance sleeve that is located at the outer side of said reciprocable stopper for movement with said reciprocable stopper and that has (1) an outlet end defining an outlet passage, (2) an opposite open end, (3) an interior female thread, and (4) at least one deflectable, anti-rotation tab which (a) projects into the longitudinal channel of said first syringe barrel to prevent rotation of said sterility maintenance sleeve relative to said first syringe barrel when said sterility maintenance sleeve is located at a predetermined longitudinal position in said first syringe barrel, and (b) deflects out of said longitudinal channel when said sterility maintenance sleeve is moved inward beyond said longitudinal channel during subsequent administration of the solution;

a removable plug for temporary insertion into said sterility maintenance sleeve through the open end of said sterility maintenance sleeve, said plug having (1) an engaging member for threadingly engaging the interior female thread of said sterility maintenance sleeve, (2) a nozzle-shaped distal end seal for sealing the outlet passage of said sterility maintenance sleeve and (3) an exterior seal wall for temporarily sealing the open end of said first syringe barrel outwardly of the longitudinal channel;

a diluent syringe for being inserted into said sterility maintenance sleeve after removal of said plug, said diluent syringe comprising
(1) a diluent syringe barrel that holds a liquid diluent and includes
(a) an exterior engaging member for threadingly engaging the interior female thread of said sterility maintenance sleeve, and
(b) a discharge end defining a discharge passage, and
(2) a movable piston plunger slidably and sealingly disposed in said diluent syringe barrel; and fluid transfer connector means for selectively accommodating transfer of liquid diluent from said diluent syringe barrel through said reciprocable stopper from the outer side of said reciprocable stopper to the inner side of said reciprocable stopper whereby the movable piston plunger of said diluent syringe can be moved toward the discharge end of said diluent syringe barrel for expressing said liquid diluent through the discharge passage of said diluent syringe barrel, through the outlet passage of said sterility maintenance sleeve, and through said reciprocable stopper via said fluid transfer connector means to combine said liquid diluent with said lyophilized drug for reconstitution of said drug in solution form whereby said removable closure can be subsequently removed from the delivery passage of said first syringe barrel and then the movable piston plunger of said diluent syringe, the diluent syringe barrel, the sterility maintenance sleeve, and the reciprocable stopper can together be moved inward so that said reciprocable stopper forces said drug solution through the delivery passage of said first syringe barrel for administration to a patient.

12. The system in accordance with claim 11 wherein
said fluid transfer connector means includes fluid communicating means comprising a resilient central portion in said reciprocable stopper and that has at least one slit defining resilient lips which are biased to a normally closed position and which can open at the inner side of said reciprocable stopper toward the delivery passage of said first syringe barrel;
said fluid transfer connector means further includes connecting means comprising:
(1) an enlarged receiving cavity defined in the central portion of said reciprocable stopper adjacent said resilient lips and a smaller entrance passage between the outer side of said reciprocable stopper and said receiving cavity whereby a retention shoulder is defined at one end of said cavity around said smaller entrance passage; and
(2) an enlarged head at said outlet end of said sterility maintenance sleeve and which is received in the enlarged receiving cavity of said reciprocable stopper whereby fluid communication through the outlet passage of said sterility maintenance sleeve is normally prevented by the resilient lips of said reciprocable stopper being in the biased closed position but is permitted when the movable piston plunger of said diluent syringe is moved inward to pressurize the liquid diluent and open said resilient lips.

13. The system in accordance with claim 12 further including a clearance space between said resilient lips and said outlet passage of said sterility maintenance sleeve.

14. The system in accordance with claim 10 wherein said venting portion of said first syringe barrel is defined by an enlarged, transverse cross section of said first syringe barrel and includes (1) spaced-apart longitudinally oriented ribs, (2) a plurality of longitudinal channels between said spaced-apart, longitudinally oriented ribs, and (3) a seal surface outwardly of said channels and ribs at said first syringe barrel open end; and
said removable plug has an enlarged transverse cross section defining a seal wall for sealingly engaging said seal surface of the venting portion of said first syringe barrel outwardly of said channels.

15. The system in accordance with claim 11 wherein
said first syringe barrel defines a plurality of longitudinal channels; and
said sterility maintenance sleeve defines a plurality of deflectable anti-rotation tabs for each being receiving in one of said channels, each of said tabs having the form of an outwardly projecting flexible finger.

16. The system in accordance with claim 11 wherein
said removable plug has a graspable portion with an enlarged cross section preventing receipt of said graspable portion in the open end of said first syringe barrel;
said graspable portion is adapted to abut said first syringe barrel at the open end of said first syringe barrel to limit the extent of insertion of said plug and sterility maintenance sleeve into said first syringe barrel; and
said graspable portion defines an exterior surface which can be grasped to rotate said removable plug and unthread the plug from said sterility maintenance sleeve.

17. The syringe system of claim 11 wherein said reciprocal stopper has a length shorter than said longitudinal channel.

18. A syringe system comprising:
a first syringe barrel for initially containing a liquid drug in an interior surface and having a delivery passage and a venting portion defining at least one longitudinal channel;
at least one rib portion in the venting portion adjacent said channel, said opposite end has a smooth portion along the inner surface between said edge and said rib portion;
a removable closure sealing closed said delivery passage; and
a reciprocable stopper initially locatable in said first syringe barrel adjacent said longitudinal channel at first position which permits passage of vapor around said reciprocable stopper through said longitudinal channel out of said first syringe barrel during lyophilization of said liquid drug, said reciprocable stopper subsequently being movable to positions inward of said channel wherein said interior surface is sealingly engaged by said reciprocable stopper for sealing the lyophilized drug in said first syringe barrel.

19. The system in accordance with claim 18 wherein
said first syringe barrel has an open end and a substantially closed end defining said delivery passage; and
said reciprocable stopper has (1) an outer side facing said first syringe barrel open end, (2) an inner side facing said first syringe barrel delivery passage, and (3) a length that is shorter than said longitudinal channel.

20. The system in accordance with claim 19 wherein
said venting portion of said first syringe barrel is defined by an offset and enlarged, transverse cross section of said first syringe barrel and includes (1) a plurality of spaced apart longitudinally oriented ribs (2) a plurality of longitudinal channels defined between said spaced-apart, longitudinally oriented ribs, and (3) a seal surface outwardly of said channels and ribs at said first syringe barrel open end; and said removable plug has an enlarged transverse cross section defining a seal wall for sealingly engaging said seal surface of the venting portion of said first syringe barrel outwardly of said channels.

21. The system in accordance with claim 19 wherein said system further includes fluid transfer connector means for accommodating fluid communication through said reciprocable stopper from the outer side of said reciprocable stopper to the inner side of said reciprocable stopper.

22. The system in accordance with claim 21 wherein said system further includes a sterility maintenance sleeve that is located at the outer side of said reciprocable stopper for movement with said reciprocable stopper and that has (1) an outlet end defining an outlet passage, (2) an opposite open end, (3) an interior female thread, and (4) at least one, deflectable, anti-rotation tab which (a) projects into the longitudinal channel of said first syringe barrel to prevent rotation of said sterility maintenance sleeve relative to said first syringe barrel when said sterility maintenance sleeve is located at a predetermined longitudinal position in said first syringe barrel, and (b) deflects out of said longitudinal channel when said sterility maintenance sleeve is moved inward beyond the longitudinal channel during subsequent administration of the drug solution.

23. The system in accordance with claim 22 wherein said fluid transfer connector means includes fluid communicating means comprising a resilient central portion in said reciprocable stopper that has at least one slit defining resilient lips which are biased to a normally closed position and which can open at the inner side of said reciprocable stopper toward the delivery passage of said first syringe barrel; and further includes connecting means comprising (1) an enlarged receiving cavity defined in said central portion of said reciprocable stopper adjacent said resilient lips and a smaller entrance passage between the outer side of said reciprocable stopper and said receiving cavity whereby a retention shoulder is defined at one end of said cavity around said smaller entrance passage; and (2) an enlarged head which is defined by said sterility maintenance sleeve at said outlet end of said sterility maintenance sleeve and which is received in the enlarged receiving cavity of said reciprocable stopper whereby fluid communication through the outlet passage of said sterility maintenance sleeve is normally prevented by the resilient lips of said reciprocable stopper being in the biased closed position but is permitted when the movable piston plunger of said diluent syringe is moved inward to pressurize the liquid diluent and open said resilient lips.

24. The system in accordance with claim 23 further including a clearance space between said resilient lips and the outlet passage of said sterility maintenance sleeve.

25. The system in accordance with claim 22 wherein said system further includes a removable plug for temporary insertion into said sterility maintenance sleeve through the open end of said sterility maintenance sleeve, said plug having (1) an exterior engaging member for threadingly engaging the interior female thread of said sterility maintenance sleeve, (2) a nozzle-shaped distal end seal for sealing the outlet passage of said sterility maintenance sleeve and (3) an exterior seal wall for temporarily sealing the open end of said first syringe barrel outwardly of the longitudinal channel.

26. The system in accordance with claim 25 wherein said system further includes a diluent syringe for being inserted into said sterility maintenance sleeve after removal of said plug, said diluent syringe including (1) a diluent syringe barrel that holds a liquid diluent and includes (a) an exterior engaging member for threadingly engaging the interior female thread of said sterility maintenance sleeve, and (b) a discharge end defining a discharge passage, and (2) a movable piston plunger slidably and sealingly disposed in said diluent syringe barrel for expressing said liquid diluent through the discharge passage of said diluent syringe barrel, through the outlet passage of said sterility maintenance sleeve, and through said reciprocable stopper by said fluid transfer connector means to combine said liquid diluent with said lyophilized drug for reconstitution of said drug in solution form whereby said removable closure can be subsequently removed from the first syringe barrel and then the movable piston plunger of said diluent syringe, the diluent syringe barrel, the sterility maintenance sleeve, and the reciprocable stopper can together be moved inward so that said reciprocable stopper forces said drug solution through the delivery passage of said first syringe barrel for administration to a patient.

27. The system in accordance with claim 26 wherein said removable plug has a graspable portion with an enlarged cross section preventing receipt of said graspable portion in the open end of said first syringe barrel;

said graspable portion is adapted to abut said first syringe barrel at said first syringe barrel open end to limit the extent of insertion of said plug and sterility maintenance sleeve into said first syringe barrel; and said graspable portion defines an exterior surface which can be grasped to rotate said plug and unthread the plug from said sterility maintenance sleeve.

28. The system in accordance with claim 22 wherein said first syringe barrel defines a plurality of longitudinal channels; and said sterility maintenance sleeve defines a plurality of flexible tabs for each being received in one of said channels, each of said tabs having the form of an outwardly projecting flexible finger.

29. The syringe system of claim 18 wherein the reciprocable stopper has a body and proximal sealing ring with a larger diameter than the body of said stopper to act as a positioning stop against said rib portion.

* * * * *

UNITED STATES PATENT AND TRADEMARK OFFICE
CERTIFICATE OF CORRECTION

PATENT NO. : 5,779,668
DATED : July 14, 1998
INVENTOR(S) : Richard W. Grabenkort It is certified that error appears in the above-identified patent and that said Letters Patent is hereby corrected as shown below:

Col. 14, line 4
 replace "said venting portion ...surface, and"
 with -- --.

Signed and Sealed this

Thirteenth Day of June, 2000

Attest:

Q. TODD DICKINSON

*Attesting Officer*     *Director of Patents and Trademarks*